United States Patent
Abraham-Fuchs et al.

(10) Patent No.: US 6,311,083 B1
(45) Date of Patent: Oct. 30, 2001

(54) METHOD FOR DETERMINING AN EXAMINATION POINT FOR THE DIAPHANOSCOPIC EXAMINATION OF A BEING AND DEVICE FOR REALIZING THE SAME

(75) Inventors: Klaus Abraham-Fuchs, Erlangen; Juergen Beuthan; Gerhard-J. Mueller, both of Berlin; Viravuth Prapavat, Hamburg, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/463,151
(22) PCT Filed: Jul. 8, 1998
(86) PCT No.: PCT/DE98/01886
    § 371 Date: May 16, 2000
    § 102(e) Date: May 16, 2000
(87) PCT Pub. No.: WO99/04684
    PCT Pub. Date: Feb. 4, 1999

(30) Foreign Application Priority Data

Jul. 21, 1997 (DE) .............................. 197 31 254

(51) Int. Cl.⁷ .................................................. A61B 5/05
(52) U.S. Cl. .......................... 600/407; 600/310; 600/473; 600/476
(58) Field of Search .................................. 600/407, 310, 600/473, 476

(56) References Cited

U.S. PATENT DOCUMENTS 4,286,602 * 9/1981 Guy .
5,452,723 9/1995 Wu et al. .
5,807,263 * 9/1998 Chance .
6,253,097 * 6/2001 Aronow et al. .

FOREIGN PATENT DOCUMENTS 0 710 832   5/1996   (EP) .

OTHER PUBLICATIONS

"Optische Diffusionstomographie zur Messung optischer Geweberparameter in der Rheumadiagnostik," Beuthan et al., Technisches Messen, vol. 63, No. 6, Jun. 1996, pp. 234–240.

"Laser Reflectance Imaging of Human Organs and Comparison with Perfusion Images," Shanthi et al., Medical & Biological Engineering & Computing, vol. 35, No. 3, May, 1997, pp. 253–258.

* cited by examiner

Primary Examiner—Marvin M. Lateef
Assistant Examiner—Runa Shah Qaderi
(74) Attorney, Agent, or Firm—Schiff Hardin & Waite

(57) ABSTRACT

In a method and an apparatus for locating an examination size for diaphanoscopic examination of a living subject, a region of the living subject wherein the optimum examination location is suspected is sequentially transilluminated with radiation, preferably in a wavelength range of the optical tissue window, for registration of scattered light distributions in the form of location-related spread functions, particularly point spread functions, and at least one function-specific, location-related feature of each spread function is determined, based on which a position value defining the examination location is determined.

30 Claims, 3 Drawing Sheets

METHOD FOR DETERMINING AN EXAMINATION POINT FOR THE DIAPHANOSCOPIC EXAMINATION OF A BEING AND DEVICE FOR REALIZING THE SAME

BACKGROUND OF THE INVENTION

1. Field of the Invention

The present invention is directed to a method for locating an examination site for conducting a diaphanoscopic examination of a living subject, as well as to an apparatus for implementing the method.

2. Description of the Prior Art

In the framework of diaphanoscopic examinations, a region of a living subject to be examined is transilluminated with light and the transillumination image that is registered is utilized for diagnosis. If one wishes to detect a pathologically induced, optical change in a specific, transilluminated volume of the life form and make the result available as the basis of the diagnosis, then the selection of an "optimum" irradiation site must assure that the pathologically modifiable tissue penetrated by the photons is maximum compared to the pathologically constant volume in order to thus be able to actually examine the region of maximum information in the scope of the main examination. This is especially important when the pathological change to be detected is small. A diaphanoscopic examination method can, for example, be implemented at a finger joint in order to make a diagnosis with regard to rheumatoid arthritis. In simplified terms, a finger joint is composed of bone tissue, cartilage tissue, skin tissue and capsular tissue as well as joint fluid. The bone tissue, cartilage tissue as well as the surrounding skin tissue thereby remain pathologically constant in the early stage; the possible pathological changes occur only in joint capsule as well as the joint fluid. In order to obtain a maximum informational content with respect to this relatively narrow diagnostic volume in the framework of the main examination, it is necessary to implement the transillumination at the optimum examination site, so that the informational content that is obtained is as great as possible. The term examination location (or examination) being a tissue location prescribable on the basis of a position value, this being illuminated by the beam crossection of the light source employed for the examination.

U.S. Pat. No. 5,452,723 discloses a spectroscopy method that is utilized in conjunction with spectroscopy of human tissue. With the method disclosed therein, the distortions of the obtained measured values are to be corrected given an examination of a thick tissue several millimeters thick due to the increased number of dispersion centers of the thick tissue compared to the spectroscopy of a very thin tissue only a few micrometers thick wherein fewer dispersion centers that influence the measured result are established. This ensues such that a spectrum of the diffuse reflectance is registered first, followed by the spectrum to be "distortion-corrected", for example the fluorescence spectrum. An effective reflectance function is subsequently determined based on probability functions. The distortion-corrected fluorescence spectrum is then determined by dividing the registered fluorescence spectrum by the effective reflectance spectrum described on the basis of the effective reflectance function. The distortions of the spectrum of the thick tissue deriving from dispersion and absorption effects as well as the geometrical and the boundary surface conditions are eliminated, the spectrum curve that is obtained corresponds in good approximation to that of a thin tissue. The "distortion-corrected" measured curve that is obtained is subsequently compared to known reference curves, and the best fit curve is identified, this being subsequently investigated in view of the presence and concentration of reference fluorophores, which is the basis for the diagnosis of the corresponding tissue property.

SUMMARY OF THE INVENTION

An object of the present invention is to provide a method with which the optimum examination location for diaphanoscopic examinations of, for example, joints can be determined.

The above object is achieved in accordance with the principles of the present invention in a method wherein a region of the life form in which the optimum examination location is suspected is sequentially transilluminated with a radiation in, preferably, a wavelength range of the optical tissue window for registering dispersed light distributions in the form of location-related spread functions, particularly point spread functions, whereby at least one function-specific, location-related feature of every spread function is identified, a position value defining the examination location being determined based thereon.

The inventive method is based on the fact that, given a (punctiform) location-dependent transillumination of the tissue to be examined, scattered light distributions in the form of spread functions arise (point spread functions given punctiform irradiation), whose change in the form of scaling over the irradiation location are a function of the light propagation and that thus enable a statement about the optical conditions of the transilluminated, overall volume. Given knowledge of the optical properties of the tissue types present in the transilluminated volume, how the photons propagate when they penetrate mainly pathologically modifiable volume can then be determined, as can the form and scaling modification in which this is presented in the resulting scattered light distribution or, respectively, spread function. Inventively, thus, different spread functions, for example five spread functions, are registered at different irradiation locations, whereupon a function-specific, location related feature is determined on the basis of the respectively obtained spread function, i.e. a diagnostic characteristic of each function. After determining these features, these are further-processed in common and, based thereon, a position value is determined that defined the optimum examination location, i.e. based whereon the optimum examination site can be determined.

For implementation, a region of the life form that covers the (expected) optimum examination site as a sub-region is transilluminated in chronological succession at a number of locations within the region. This, for example, can ensue in equidistant steps along a line, for instance parallel to the longitudinal axis of a finger (called x-axis below). A radiation in the wavelength range of the optical tissue window is preferably employed. Upon penetration of the tissue, the incoming light, which is (approximately) punctiform, is dispersed. The spatial distribution of the scattered light is acquired with a planar or line-shaped arrangement of light detectors. The intensity of the scattered light measured in this way as function of the location of the light detectors is referred to as a scattered light distribution function or also, more specifically, as a (point) spread function. For example. Eugene Hecht, "Optik", Addison-Wesley-Verriag, 1989, pp. 512 ff., is referenced for more detailed explanation of the term "spread function". The shape of the course of this spread function is dependent on the composition of the transirradiated tissue and, thus, is dependent on the selected irradiation location. A separate, characteristic spread function is thus obtained for each sequentially selected irradiation location. In general, function curves can be described ("parameterization" of a function) by one or more characteristic values (function-specific parameters or features), for example maximum value of the function, location of the maximum value of the function, location of the maximum slope or curvature of the function, etc. For the method disclosed herein, at least one or a mathematical operation of a number of description parameters of the function is selected, this being characteristic of the modification of the spread function given variation of the irradiation location, particularly for the differences in the form of the spread function given transirradiation of healthy and sick tissue. These parameters for describing the function curve of the measured spread functions are referred to below as function-specific, location-related features (related to the location of irradiation). The comparison of the values of these parameters then enables the selection of the irradiation location or optimum examination location that contains the most information about the pathological modification of the tissue.

For example, location parameters, i.e. x-values, of the spread function with respect to distinguished points of the spread function can thus be determined as location-related, function-specific features and can be subsequently further-processed.

For example, the respective position values, i.e. the x-values, of the maximums and/or of the centers of gravity of the spread functions can be inventively employed as features. The position value defining the examination location can thereby be inventively determined by forming the average from the position values of the maximums or of the centers of gravity. As has been shown in the framework of trials, the scattered light distributions that are obtained differ in diagnostic utility dependent on how close the respective irradiation location lies to the optimum examination location. Taking the optical properties of this tissue into consideration, it can be assumed that there is a high probability of finding a suitable irradiation location where the overall irradiation intensity (area of the resulting scattered light distribution) is high and the width of the resulting scattered light distribution is narrower compared to the distributions that exist given irradiation around this point. The informational content with respect to the individual spread functions in view of the determination of the examination location is thus respectively different. In order to counter this, an expedient development of the inventive idea provides that each function-specific, location-related feature is weighted with a weighting factor that can be expediently determined based on at least one, and possibly on more, function-specific features. By taking this weighting factor into consideration, thus, each spread function contributes differently to the identified position value, i.e. the function lying closer to or at the optimum examination location enters in significantly more strongly than those lying therebeside. Expediently, the weighting factor can be multiplicatively determined from the overall irradiation intensity and the standard deviation of each spread function, since the probability is high of finding a suitable irradiation location where the overall radiation intensity is high and the width of the scattered light distribution is low compared to distributions around this point. The weighting factors, further, can be normed to the highest identified weighting factor.

The optimum examination site can be identified with adequate precision with the described determination method of the position value by averaging, potentially by weighted averaging, in order to be able to implement a diagnostically relevant examination. The determination of this examination site, however, ensues at the detector side since the spread functions that are obtained are determined at the detector side and the position values that are obtained are acquired from this information of the detector side. When, due to the physiological conditions of the transilluminated volume, the irradiation sites noticeably deviate from the identified, location-related position values obtained from the spread functions, the position value determined approximately at the detector side can be too imprecise in order to directly transfer it onto the irradiation plane. Given, for example, a finger joint, this can be produced in that the capsule tissue and the joint fluid have light-conducting properties and light coupled in here is in turn coupled out with priority at a specific position. In order to counter this in a further embodiment of the invention, after determining the position value, a back-transformation ensues into the irradiation plane. This can be expediently realized by determining a further position value for the back-transformation, the first position value that is determined and that refers to the detector side being shifted by this further position values. In other words, a correction value is determined as the further position value, this correction value compensating the offset between the irradiation location and the identified, first position value caused by the physiological conditions and being employed for the corresponding shift of the identified, first position value, so that the position value obtained as a result thereof characterizes the irradiation location in the irradiation plane. The offset between the irradiation-side irradiation location of the spread function with the highest overall irradiation intensity or the highest weighting factor and the detector-side position of the function maximum or of the center of gravity of this spread function can be inventively employed as further position value.

The position datum or data can be inventively determined on the basis of the directly obtained spread functions or on the basis of a spread function smoothed at least in the region of the maximums, insofar as the course of the curve allows a corresponding determination exhibiting an acceptable error. When this is not possible with an acceptable error, in a further embodiment of the invention the spread functions that are obtained are approximated by means of respective approximation functions, and the position value or values are determined on the basis of the approximation functions. Expediently, each spread function can be approximated with one or more Gaussian functions.

In addition to being directed to the inventive method, the invention is also directed to an apparatus for the implementation of the method. This apparatus an irradiation unit, a detector, a control unit and a computer, and the computer is fashioned for the determination of an optimum examination location according to the above-described method, and the control unit is fashioned for the control of the irradiation unit dependent on the determination result. Inventively, the irradiation unit can include a radiation source for a specific wavelength, and positioning unit controllable by the control unit can be provided for moving the radiation source. In this first embodiment of the invention, only one radiation source is utilized, this being moved via the corresponding positioning unit to the optimum examination site after determination thereof. Alternatively, the irradiation unit can include a number of radiation sources respectively for specific wavelengths that can be separately driven with the control unit. Positioning of the radiation sources is not absolutely required if this embodiment of the irradiation unit is fashioned grid-like, particularly when the grid dimension, i,e. the spacing of the radiation sources from one another, is selected adequately small. When the grid dimension is relatively coarse, a positioning unit can be inventively provided for moving at least one, preferably all radiation sources, the positioning unit being controllable via the control unit dependent on the determination result. Operation without a positioning unit can ensue, for example, by employing a grid of radiation sources that are closely spaced to each other within the grid, with only specific radiation sources, disposed at larger distances from each other within the grid, being energized for emitting radiation to determine the examination site. After determining the optimum examination site, another radiation source, which lies optimized relative to the optimum examination site due to the very small grid, can then be driven. The grid dimension of the radiation sources and the diameter of the respectively emitted light beam should have a ratio of approximately 1:1 through approximately 3:1, particularly 2:1. When the radiation sources are movable, a grid dimension of the radiation sources of approximately 250 μm through 750 μm, preferably 500 μm,, has proven expedient, whereby the beam diameter here should amount to approximately 125 μm through 500 μm, particularly 250 μm. Given immobile radiation sources, the grid dimension should be optimally small and lie in a range from approximately 125 μm through 500 μm, particularly at 250 μm. In order to locate the optimum examination site while also allowing the examination to be conducted at a number of wavelengths, which definitely leads to results with greater diagnostic utility, a number of radiation sources for respectively difficult wavelengths can be provided in the inventive apparatus.

DESCRIPTION OF THE PREFERRED EMBODIMENTS

Figure 3:
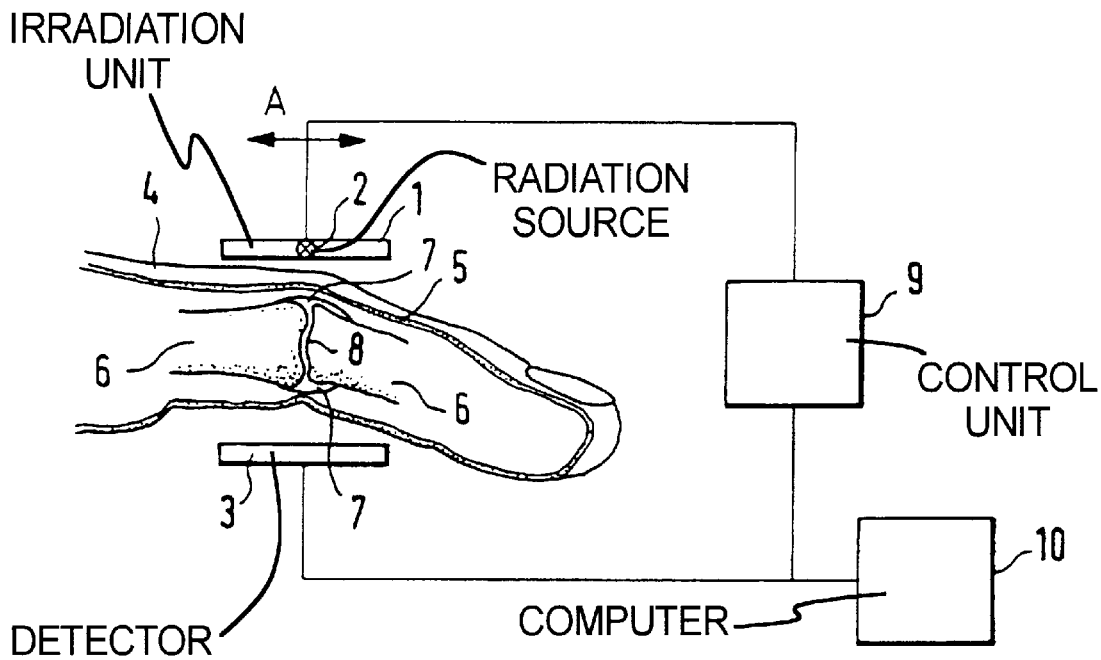
FIG. 3 is a schematic block diagram of a first embodiment of an inventive apparatus.

For a better understanding of the determination method described below with reference to an exemplary embodiment, the inventive apparatus for the implementation of this method, as shown, for example, in FIG. 3, will be described first. This apparatus is composed of an irradiation unit 1, for example in the form of a laser with a wavelength of 675 nm. A detector 3 is provided thereopposite. The region of a living subject to be examined, a finger 4 in the illustrated example, is placed between irradiation unit 1 and detector 3. In the region of a joint to be examined, this finger 4 is composed of skin tissue 5, cartilage and bone tissue 6 as well as joint capsule tissue 7 and joint fluid 8. A control unit 9 controls the operation and a computer 10 determines the optimum examination location from the data obtained by the detector 3. Given this embodiment having only one radiation source 2, the operation for determining the optimum examination location ensues such that the irradiation unit 1 together with the radiation source 2 is moved, for example, to five selected positions above the joint gap, whereby the mobility is indicated by the double arrow A. The positioning unit required for this purpose is not explicitly shown. A punctiform transillumination of the tissue then ensues at each of the selected locations. The respective scattered light distribution for each irradiation is registered with the detector 3 in the form of a point spread function and is supplied to the computer means 10, which, on the basis of the method described below, determines the optimum examination site and supplies a signal indicating this site to the control unit 9, which then causes the irradiation unit 1 to be driven and moved for the implementation of the actual examination.

Figure 1:
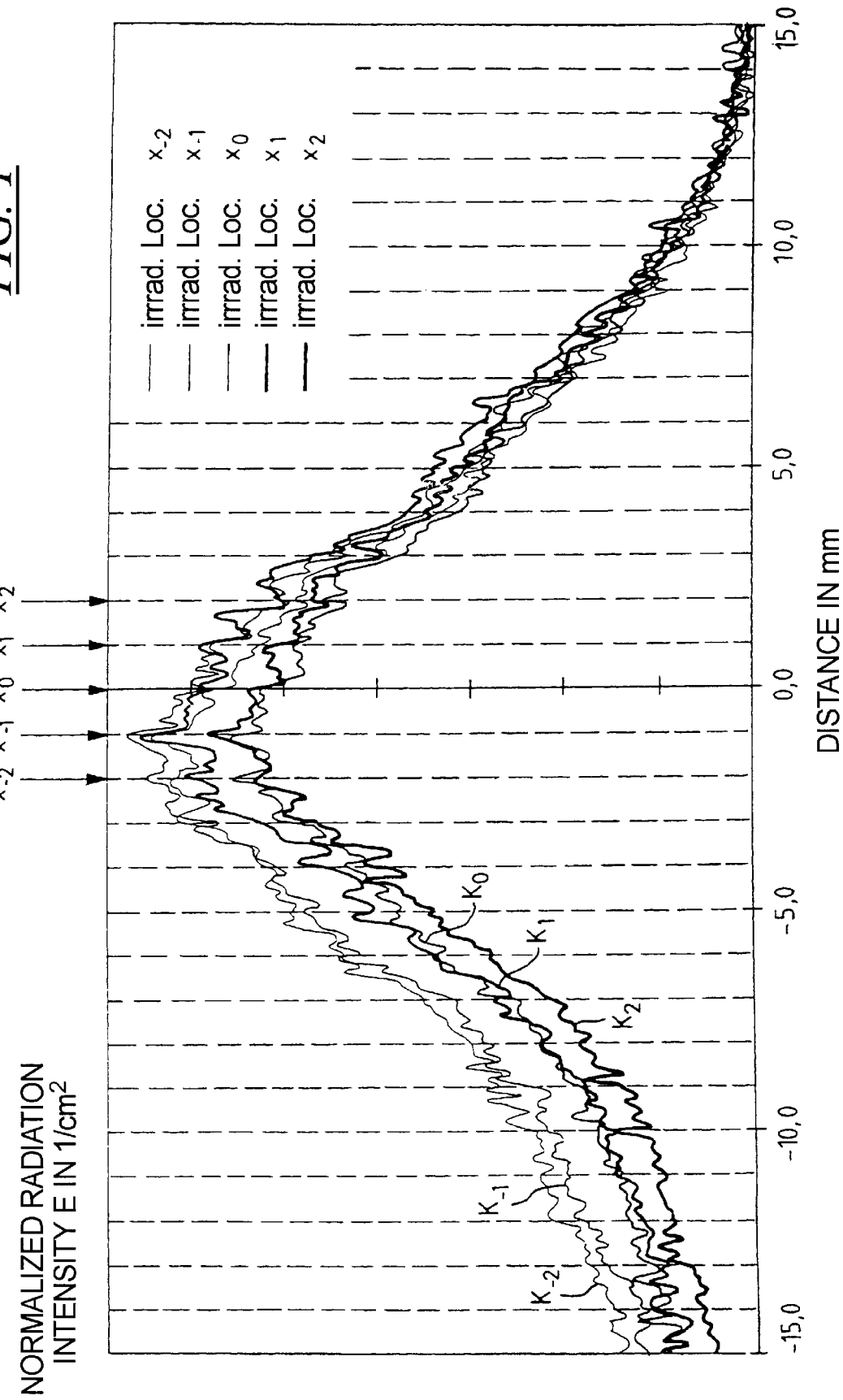
FIG. 1 is a graph showing five scattered light distributions obtained in accordance with the invention.
Figure 2:
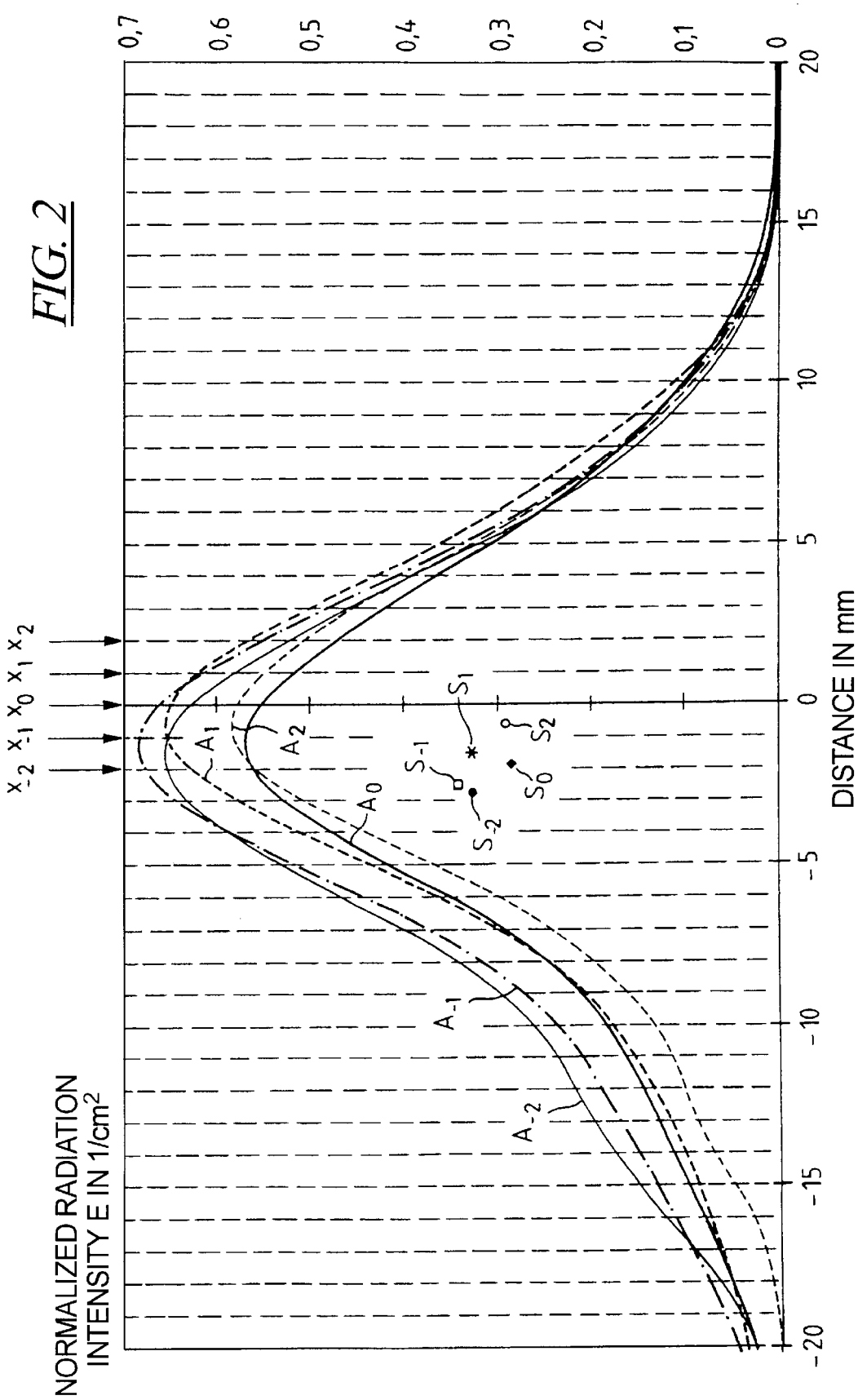
FIG. 2 shows five approximation curves calculated for the scattered light distributions of FIG. 1, as well as the respective centers of gravity associated therewith.

As already described, the scattered light distribution is registered for each of the predetermined irradiation locations around a defined zero position. Such scattered light distributions are shown in FIG. 1, wherein the location in mm around the zero position is indicated along the abscissa and the normalized irradiation intensity is indicated in $1/cm^2$ along the ordinate. The arrows respectively indicate the irradiation location for the respective curves. The irradiation locations shown here lie distributed ±2 millimeters around the zero location, i.e. a total of five irradiation locations were selected. The respectively obtained scattered light distribution for each of the irradiation locations $X_{-2} \ldots X_2$ is indicated with the reference characters $K_{-2} \ldots K_2$. As can be derived from FIG. 1, the course of the curve is still relatively noise-infested and allows only an inexact determination of the optimum examination location. To this end, an approximation curve $A+_2 \ldots A_{+2}$ is determined for each of the curves $K_{-2} \ldots K_{+2}$ by approximation with a number of Gaussian functions. These approximation curves are shown in FIG. 2. Moreover, the respective centers of gravity $S_{-2} \ldots S_{+2}$ of the curves are also determined for each curve $A_2 \ldots A_2$. The centers of gravity are not utilized for the determination of examination sites described below; however, the determination method could likewise be implemented based on these values.

A series of function-specific, location-related features are then determined for determining the optimum examination location, as can be derived from the following table.

TABLE

| irradiation location (in mm) | $X_{-2} =$ <br> −2 mm | $X_{-1} =$ <br> 1 mm | $X_0 =$ <br> 0 mm | $X_1 =$ <br> 1 mm | $X_2 =$ <br> 2 mm |
|---|---|---|---|---|---|
| x-value of $E_{max}$ (in mm) | −1.6 | −1.4 | −1.2 | −0.6 | −0.8 |
| Overall irradiation intensity $E_{ges}$ | 50.0 | 50.8 | 42.4 | 47.0 | 39.7 |
| Standard deviation s | 6.898 | 6.793 | 6.74 | 6.807 | 5.914 |
| Weighting factor W = $E_{ges}*s$ | 329.9 | 345.08 | 285.13 | 319.93 | 234.8 |
| Normed weighting factor | 0.956 | 1 | 0.826 | 0.927 | 0.680 |
| Weighted x-value of $E_{max\,(in\,mm)}$ | −1.53 | −1.4 | −0.99 | 0.56 | 0.54 |

The x-values of the respective curve maximums $E_{max}$ are first determined on the basis of the approximation functions. As can be derived from line 2 of the Table, these respectively lie in the negative range. It is already possible to calculate a first examination location from these values by averaging. This would lie at $X_{average}=1.12$ mm.

For taking the actual amount of the scattered light distributions into consideration, it is expedient to determine a weighting factor and to take it into consideration in the formation of the average. Certain properties of the scattered light distribution such as the overall irradiation intensity $E_{gea}$ (=area under the respective curve) and the standard deviation (=width of the curve) are available for calculating this weighting factor. The values therefor determined with respect to the approximation function can be derived from lines 3 and 4. Based thereon, it is possible to multiplicatively determine a weighting factor from these two values, whereby the values are recited in line 5. Subsequently, the identified weighting factor is normalized to the highest weighting factor (line 6). When the identified x-values of $E_{max}$ (column 2) are now multiplied by the normalized weighting factors, then the weighted x-values of $E_{max}$ are obtained, as indicated in line 7. The weighted average that can be calculated from these weighted values amounts to $x_{average}$=1.004 mm and takes the respective amount of the individual scattered light distributions into account. Compared to the position value calculated unweighted, a difference of 0.116 mm thus derives.

Subsequently, the weighted average that specifies the optimum location at the detector side must be back-transformed onto a coordinate of the excitation side. To this end, the offset between the irradiation location that supplies the highest weighting factor, or the highest $E_{ges}$, and the position of $E_{max}$ of this scattered light distribution is employed In the illustrated exemplary embodiment, the irradiation position that supplies the scattered light distribution with the highest weighting factor is the irradiation location $X_1$. The $E_{max}$-position of this scattered light distribution is $X_{Emax}$=1.4 mm. An offset of $X_1-X_{Emax}$=1 mm−(−1.4 mm) +0.4 mm derives therefrom. For back-transformation, the calculated, weighted average of 1.004 mm is shifted by this offset, so that the new zero position in the irradiation plane is selected as $X_{optimum}$=0.604 mm.

Instead of employing the x-values of $E_{max}$, the disclosed determination method can be implemented in the same way based on the centers of gravity of the respective approximation functions.

Figure 4:
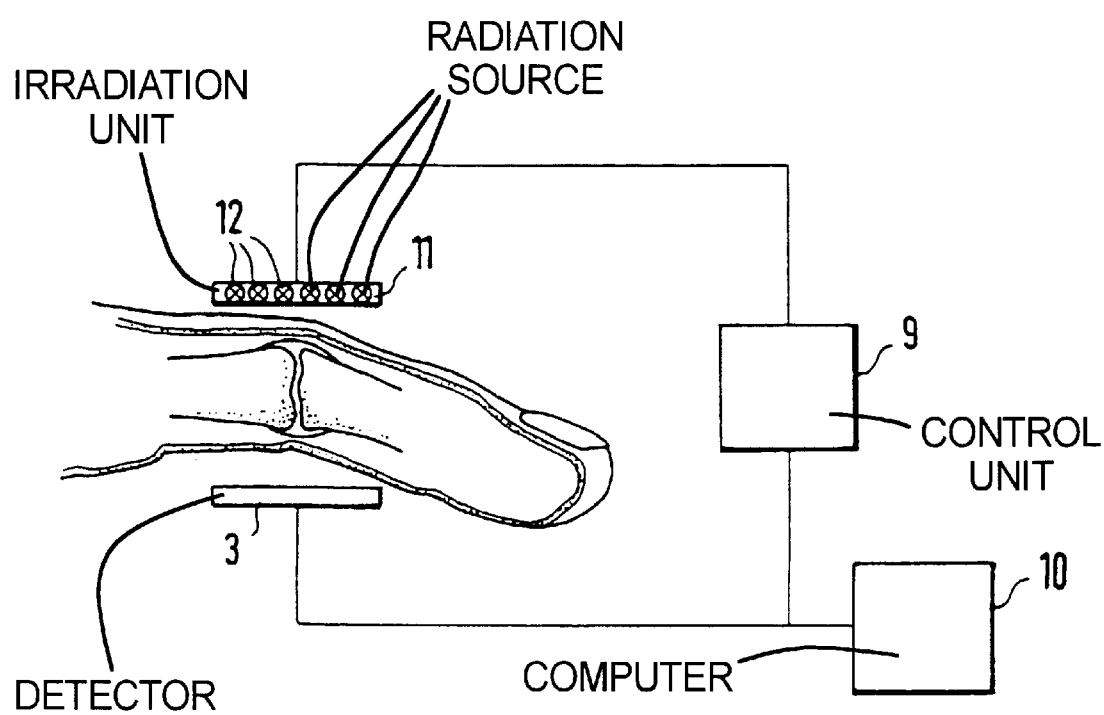
FIG. 4 is a schematic block diagram of a second embodiment of an inventive apparatus.

Finally, FIG. 4 shows a further embodiment of an inventive apparatus. The structure is largely the same as shown in FIG. 3; however, an irradiation unit 11 is employed in this embodiment that contains a number of radiation sources 12. The radiation sources 12 are spaced from one another grid-like, whereby a grid of 500 $\mu$m or less, preferably 250 $\mu$m, is employed. In the illustrated exemplary embodiment, only seven radiation sources are indicated for clarity; the number, of course, is substantially greater in view of the selected grid spacing. The operation of this apparatus is such that, for example, only every other radiation source 12 is driven, whereby, of course, only those are driven that are in a correspondingly close position to the suspected, optimum examination site. After determining the optimum examination site, a radiation source 12 that is more beneficial because it lies closer to the examination location can then be driven via the control unit 9, which is also present in this embodiment. Such an operation is possible given an adequately small spacing, for example 250 $\mu$m, Insofar as a larger grid spacing is selected (for example, 500 $\mu$m), it is likewise conceivable to provide for positioning of the irradiation unit 11 in order to move a selected radiation source to the optimum examination location.

Although modifications and changes may be suggested by those skilled in the art, it is the intention of the inventors to embody within the patent warranted hereon all changes and modifications as reasonably and properly come within the scope of their contribution to the art.

What is claimed:

1. A method for locating an examination site for conducting a diaphanoscopic examination of a living subject, comprising the steps of:
successively transilluminating a region of an examination subject with radiation in a wavelength range of an optical tissue window of said region;
detecting a plurality of scattered light distributions, each represented as location-dependent spread functions, respectively for said transilluminations of said region;
for each of said spread functions, identifying at least one function-specific, location-dependent feature, and thereby obtaining a plurality of determined features; and
from said plurality of determined features, identifying a position value for an examination site within said region for subsequently conducting a diaphanoscopic examination.

2. A method as claimed in claim 1 comprising selecting said function-specific, location-dependent feature from the group consisting of a position value of a maximum and a position value of a center of gravity.

3. A method as claimed in claim 1 wherein the step of determining said examination site comprising averaging the function-specific, location-dependent features of the respective spread functions.

4. A method as claimed in claim 1 wherein the step of determining said examination site comprises weighting said function-specific, location-dependent features of the respective spread functions with respectively different weighting factors, to obtain a plurality of weighted features, and determining said position value of said examination site from said weighted features.

5. A method as claimed in claim 4 comprising determining said weighting factors respectively from at least one further function-specific feature of the spread function to which the weighting factor is applied.

6. A method as claimed in claim 5 wherein each of said spread functions has an overall radiation density and a standard deviation, and comprising determining each weighting factor by multiplying the overall radiation density and the standard deviation of the spread function to which the weighting factor is applied.

7. A method as claimed in claim 5 wherein said weighting factors consist of a highest weighting factor and a plurality of other weighting factors, and comprising the additional step of normalizing all of said other weighting factors relative to said highest weighting factor.

8. A method as claimed in claim 1 wherein said region is successively transilluminated in an irradiation plane, and comprising the additional step of back-transforming said position value into said irradiation plane.

9. A method as claimed in claim 8 comprising, for back transforming said position value into said irradiation plane, determining a further position value and back-transforming said position value into said irradiation plane by shifting said position value dependent on said further position value.

10. A method as claimed in claim 9 wherein said region has an irradiation side, at which said radiation is incoming, and a detection side, at which said radiation is detected after passing through said region, and comprising determining said further position value by the steps of:
identifying a spread function, among said plurality of spread functions, having a highest overall radiation intensity, as a highest-intensity spread function;
identifying a location of a maximum of said highest-intensity spread function at said irradiation side of said region, as a first location, and identifying a location of a maximum of said highest-intensity spread function at said detection side of said region, as a second location; and
determining said further position value as an offset between said first location and said second location.

11. A method as claimed in claim 9 wherein said region has an irradiation side, at which said radiation is incoming, and a detection side, at which said radiation is detected after passing through said region, and comprising determining said further position value by the steps of:
identifying a spread function, among said plurality of spread functions, having a highest overall radiation intensity, as a highest-intensity spread function;

identifying a location of a center of gravity of said highest-intensity spread function at said irradiation side of said region, as a first location, and identifying a location of a center of gravity of said highest-intensity spread function at said detection side of said region, as a second location; and determining said further position value as an offset between said first location and said second location.

12. A method as claimed in claim 9 wherein said region has an irradiation side, at which said radiation is incoming, and a detection side, at which said radiation is detected after passing through said region, and wherein said further position value is determined by the steps of:

determining a plurality of weighting factors respectively for said function-specific, location-dependent features, said weighting factors including a highest weighting factor;

identifying a spread function having a highest weighting factor, as a highest weighting factor spread function;

identifying a location of a maximum of said highest weighting factor spread function at said irradiation side of said region, as a first location, and identifying a location of a maximum of said highest weighting factor spread function at said detection side of said region, as a second location; and determining said further position value as an offset between said first location and said second location.

13. A method as claimed in claim 9 wherein said region has an irradiation side, at which said radiation is incoming, and a detection side, at which said radiation is detected after passing through said region, and wherein said further position value is determined by the steps of:

determining a plurality of weighting factors respectively for said function-specific, location-dependent features, said weighting factors including a highest weighting factor;

identifying a spread function having a highest weighting factor, as a highest weighting factor spread function;

identifying a location of a center of gravity of said highest weighting factor spread function at said irradiation side of said region, as a first location, and identifying a location of a center of gravity of said highest weighting factor spread function at said detection side of said region, as a second location; and determining said further position value as an offset between said first location and said second location.

14. A method as claimed in claim 1 wherein each of said spread functions has a maximum, and comprising the step of smoothing each of said spread functions, at least in a region of the maximum thereof, before determining the respective function-specific location-dependent features of said spread functions.

15. A method as claimed in claim 1 comprising approximating said spread functions, with respective approximation functions, before determining said function-specific, location-dependent features of the respective spread functions.

16. A method as claimed in claim 15 comprising approximating said spread functions with Gaussian approximation functions.

17. A method as claimed in claim 1 comprising representing said scattered light distributions respectively as point spread functions.

18. An apparatus for locating an examination site for conducting a diaphanoscopic examination of a living subject, comprising the steps of:

a radiation unit for successively transilluminating a region of an examination subject with radiation in a wavelength range of an optical tissue window of said region;

a radiation detector disposed for detecting a plurality of scattered light distributions, each represented as location-dependent spread functions, respectively for said transilluminations of said region;

a computer supplied with said spread functions which, for each of said spread functions, identifies at least one function-specific, location-dependent feature, thereby obtaining a plurality of determined features, and which from said plurality of determined features, identifies a position value for an examination site within said region for subsequently conducting a diaphanoscopic examination.

19. An apparatus as claimed in claim 18 wherein said irradiation unit comprises a radiation source which emits said radiation at a single wavelength, and further comprising a positioning unit, operated by said control unit, for moving said radiation source relative to said region to successively transilluminate said region from a plurality of different positions.

20. An apparatus as claimed in claim 18 wherein said irradiation unit comprises a plurality of separate radiation sources, respectively operating at a same wavelength, disposed at a plurality of different positions relative to said region, and individually driven by said control unit.

21. An apparatus as claimed in claim 20 comprising a positioning unit, operated by said control unit, for moving at least one of said radiation sources dependent on said position value.

22. An apparatus as claimed in claim 20 wherein said radiation sources are respectively disposed in said radiation unit in a grid having a grid spacing, and wherein each of said radiation sources emits said radiation in a beam having beam diameter, and wherein a ratio of said grid spacing to said beam diameter is in a range between approximately 1:1 through approximately 3:1.

23. An apparatus as claimed in claim 22 wherein said ratio is 2:1.

24. An apparatus as claimed in claim 22 wherein said grid spacing is in a range between approximately 250 $\mu$m through approximately 750 $\mu$m, and wherein said beam diameter is in a range between approximately 125 $\mu$m through approximately 5000 $\mu$m.

25. An apparatus as claimed in claim 24 wherein said grid spacing is approximately 500 $\mu$m.

26. An apparatus as claimed in claim 24 wherein said beam diameter is approximately 250 $\mu$m.

27. An apparatus as claimed in claim 22 wherein said grid spacing is in a range between approximately 125 $\mu$m through approximately 500 $\mu$m, and wherein said beam diameter is in a range between approximately 125 $\mu$m through approximately 500 $\mu$m.

28. An apparatus as claimed in claim 27 wherein said grid spacing is approximately 250 $\mu$m.

29. An apparatus as claimed in claim 27 wherein said beam diameter is approximately 250 $\mu$m.

30. An apparatus as claimed in claim 18 wherein said irradiation unit comprises a plurality of radiation sources respectively emitting radiation at different wavelengths in said wavelength range.

\* \* \* \* \*